US00PP08064P

United States Patent [19]

Twomey

[11] Patent Number: Plant 8,064

[45] Date of Patent: Dec. 22, 1992

[54] ROSE PLANT NAMED 'TWOMIN'

[75] Inventor: Jerry Twomey, Leucadia, Calif.

[73] Assignee: DeVor Nurseries, Inc., Watsonville, Calif.

[21] Appl. No.: 652,417

[22] Filed: Feb. 6, 1991

[51] Int. Cl.[5] ..... A01H 5/00

[52] U.S. Cl. ..... Plt./10

[58] Field of Search ..... Plt./10

*Primary Examiner*—James R. Feyrer

*Attorney, Agent, or Firm*—Christie, Parker & Hale

[57] ABSTRACT

A new miniature market class rose plant producing orange red flowers.

1 Drawing Sheet

SUMMARY OF THE INVENTION

The present invention relates to a new and distinct variety of rose plant of the miniature rose class, which was originated by my crossing as seed parent and pollen parents two unnamed and unpatented seedlings of my creation which, although have hybrid tea in their heritage, conform best to the miniature market class. The varietal denomination of this new rose is "Twomin".

Among the novel characteristics possessed by this new variety which primarily distinguishes it from its parents and all other varieties of which I am aware are its unusual orange red flowers which open well upon aging. The new variety is especially suited for growing in outdoor gardens and exhibits improved vigor and flower production. The plant blooms freely under natural conditions.

Asexual reproduction by propagation by budding and rooting cuttings of the new variety, as performed in Pleasanton, Calif. and Watsonville, Calif., shows that the foregoing and other distinguishing characteristics come true to form and are established and transmitted through succeeding propagations.

BRIEF DESCRIPTION OF ILLUSTRATION

The accompanying illustration shows a typical specimen of the flower and vegetative growth of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color descriptions herein refer to plate numbers in the aforementioned color chart.

Parentage: Seedling.

*Seed parent.*—Unnamed seedling.

*Pollen parent.*—Unnamed seedling.

Class: Miniature.

The following observations are made of specimens grown under glass in Watsonville, Calif.

Flower

Blooming habit: Continuous.

A. Bud:

(1) *Size.*—About 2 cm diameter and about 1.5 cm long.

(2) *Form.*—Ovoid.

(3) *Color.*—As sepals divide, near 43A.

(4) *Sepals.*—Longer than bud, simple to foliated; Inside — near 183C with near 147C at base; Outside — near 187A.

(5) *Peduncle.*—Length — about 3.0 to 4.0 cm with very small prickles Aspect — near straight Strength — erect, slender Color — near 146B.

(6) *Calyx.*—Smooth, funnel-shaped, does not split; 0.9 cm×0.8 cm.

B. Bloom:

(1) *Size.*—Average size when fully expanded — about 7.0 cm; depth about 1.5 cm.

(2) *Borne.*—Usually in clusters of 7 to 10, sometimes singly.

(3) *Form.*—Cupped at first, becoming flat; outer petals slightly curled and somewhat lobed; pointed apices predominate on inner petals especially as blooms age.

(4) *Petalage.*—Under normal conditions average is about 30 to 40.

(5) *Color.*—After sepals fall and petals begin to unfurl, flower coloring appears fairly constant near 43A to 44A with the deeper tonality at outer petals. Petal undersurface is of similar coloration to upper surface, though it may be slightly lighter. General tonality from a distance is attractive orange red. Color of petal at point of attachment is near 1B.

(6) *Lasting Quality.*—Long lasting on the plant.

C. Petals:

(1) *Texture.*—Slightly-leathery.

(2) *Appearance.*—Inside velvety and outside satiny.

(3) *Form.*—Broad, fan shaped with pointed apices or undulating or curved margins.

(4) *Arrangement.*—Regularly arranged, imbricated.

(5) *Petaloids in center.*—Approximately 12.

(6) *Persistence.*—Persist.

(7) *Fragrance.*—Very slight.

Reproductive Organs

A. Stamens, filaments and anthers:

*Arrangement and color.*—Stamens antrorse, about 53; anthers about 0.3 cm, near 20A; filaments 0.5–0.6 cm, near 39B changing to near 20A.

B. Pistils: About 46.

C. Pollen:

*Color.*—Near 20A.

D. Styles: Medium length, even; 0.7 cm, color is near 1C.

E. Stigmas:

*Color.*—Near 19C.

F. Ovaries: Round with silver hairs covering.

Plant

A. Form: Upright, compact.

B. Growth: Moderate, free branching.

*Height attained.*—About 68 to 70 cm average.

C. Foliage: Compound 3, 5 and 7 leaflets.

(1) *Size.*—Medium.

(2) *Quantity.*—Abundant.

(3) *Color.*—Upper side — near 147A. Under side — near 147B.

(4) *Shape.*—Oval, pointed, leaf size about 8.5 cm × about 9.0 cm.

(5) *Texture.*—Upper side — semi-leathery. Under side — matte.

(6) *Edge.*—Serrate, (denticulate).

(7) *Serration.*—Ordinary.

(8) *Leaf stem.*—Color — medium green.

(9) *Stipules.*—Adnate tipped with small glands.

(10) *Rachis.*—6 cm on 3 leaf; 8.5 to 9.0 cm on 5 leaf; 8.5 to 9.0 cm on 7 leaf.

(11) *Petioles.*—Length — 1.0 on 3 leaf and 7 leaf; 1.5 cm on 5 leaf.

(12) *Ribs and veins.*—Very slightly depressed on top, rounded slightly underneath. Rachis: Small spines underneath.

(13) *Resistance to disease.*—Moderate resistance to mildew, blackspot and rust.

D. Wood:

*Color.*—Medium green.

*Bark.*—Smooth.

E. Thorns:

(1) *Thorns.*—Quantity (main stalk) — ordinary. Form — pointed, thin, declining. Length — about 0.3 to 0.4 cm. Color — near 187A. Position — irregular.

(2) *Prickles.*—Few to none.

F. Winter hardiness: Needs protection in severe climates.

I claim:

1. A new and distinct variety of rose plant of the miniature rose class, substantially as shown and described.

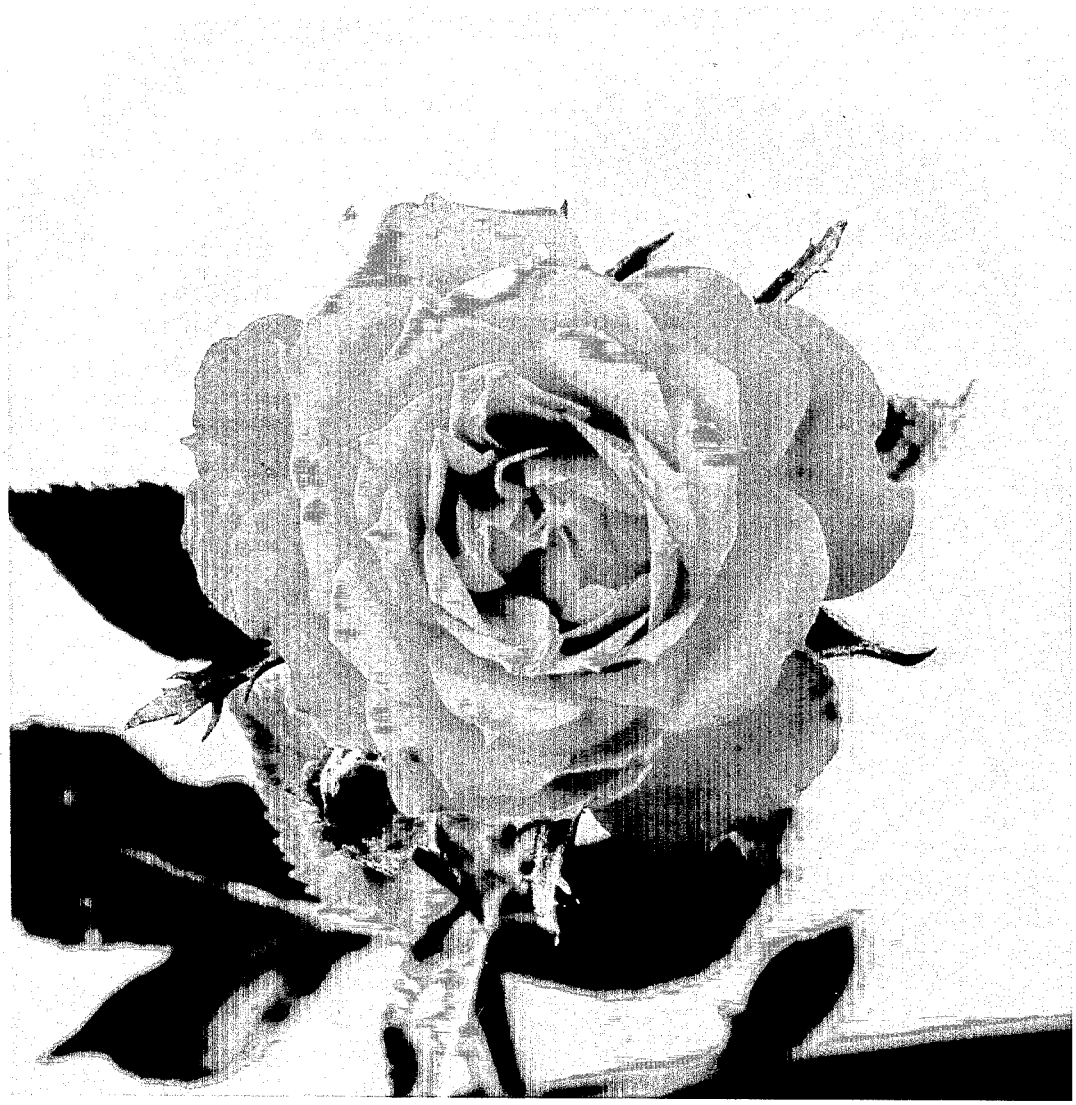

* * * * *